US012638434B2

(12) United States Patent
Sui et al.

(10) Patent No.: US 12,638,434 B2
(45) Date of Patent: May 26, 2026

(54) EVALUATION METHOD OF DUCTILITY OF GROUTED ROCK MASS FOR ADVANCED RENOVATION OF WATER-SAND MIXTURE INRUSH AREA

(71) Applicants:China University of Mining and Technology, Xuzhou (CN); 2th Exploration Team of Jiangsu Coal Geological, Xuzhou (CN)

(72) Inventors: Wanghua Sui, Xuzhou (CN); Chang Zhou, Xuzhou (CN); Shichong Yuan, Xuzhou (CN); Yuan Hang, Xuzhou (CN); Shuangcheng Tang, Xuzhou (CN); Baolei Xie, Xuzhou (CN)

(73) Assignees: China University of Mining and Technology, Xuzhou (CN); Exploration Team of Jiangsu Coal Geological, Xuzhou (CN)

( * ) Notice: Subject to any disclaimer, the term of this patent is extended or adjusted under 35 U.S.C. 154(b) by 277 days.

(21) Appl. No.: 18/235,899

(22) Filed: Aug. 21, 2023

(65) Prior Publication Data

US 2024/0159150 A1     May 16, 2024

(30) Foreign Application Priority Data

Nov. 4, 2022    (CN) .......................... 202211376588.1

(51) Int. Cl.
| | |
|---|---|
| *G01N 33/24* | (2006.01) |
| *C04B 111/70* | (2006.01) |
| *E02D 1/00* | (2006.01) |
| *E21F 17/18* | (2006.01) |

(52) U.S. Cl.
CPC ............... *G01N 33/24* (2013.01); *E02D 1/00* (2013.01); *C04B 2111/70* (2013.01); *E21C 2100/00* (2023.05); *E21F 17/18* (2013.01)

(58) Field of Classification Search
CPC ....... G01N 33/24; E02D 1/00; C04B 2111/70; E21C 2100/00; E21F 17/18
See application file for complete search history.

(56) References Cited

PUBLICATIONS

Effect of grouting on damage and fracture characteristics of fractured rocks under mode I loading; Hu et al. 2024 (Year: 2024).*

(Continued)

*Primary Examiner* — Ryan D Walsh
(74) *Attorney, Agent, or Firm* — Gearhart Law LLC

(57) ABSTRACT

Provided is an evaluation method of ductility of a grouted rock mass for advanced renovation of a water-sand mixture inrush prevention area including following steps: first, acquiring a spatial distribution law of cracks in overlying strata, and establishing a three-dimensional geological model and a grouted rock mass unit geological model; calculating rock mass quality standard of the target rock strata; performing compression tests on multiple groups of grouted consolidated bodies, and calculating an average value of strain softening indexes of the multiple groups of grouted consolidated bodies; selecting multiple groups of grouted target rock strata, and calculating an average value of unstable fracture ductility of the multiple groups of grouted target rock strata; finally, acquiring a permeability strength of the grouted rock mass, and calculating and grading an evaluation index of ductility of the grouted rock mass.

3 Claims, 1 Drawing Sheet

(56)                        References Cited

PUBLICATIONS

Effect of grouting on shear behavior of rock joint; Salimian et al; 2017 (Year: 2017).*

Experimental and numerical study on the mechanical properties of compressively precracked sandstone repaired by grouting; Zhang et al.; 2022 (Year: 2022).*

Experimental Study on the Mechanical Properties of Cracked Limestone Reinforced by Modified Cement Grouting; Zhu et al.; 2025 (Year: 2025).*

Shaojie Ma et al., "Grouting Material for Broken Surrounding Rock and its Mechanical Properties of Grouting Reinforcement", Geotech Geol Eng (2021) 39:3785-3793, Published on Feb. 24, 2021, available at: https://doi.org/10.1007/s10706-021-01725-y(01234567-89().,-vo, pp. 9.

Wenqiang Mu et al., "Numerical calculation and multi-factor analysis of slurry diffusion in an inclined geological fracture", Hydrogeology Journal (2020) 28:1107-1124, Published on Jan. 16, 2020, available at: https://doi.org/10.1007/s10040-019-02103-y, pp. 18.

Jiateng Guo et al., "Three-dimensional geological modeling and spatial analysis from geotechnical borehole data using an implicit surface and marching tetrahedra algorithm", Engineering Geology 284 (2021) 106047, Published on Feb. 12, 2021, available at: https://doi.org/10.1016/j.enggeo.2021.106047, pp. 14.

* cited by examiner

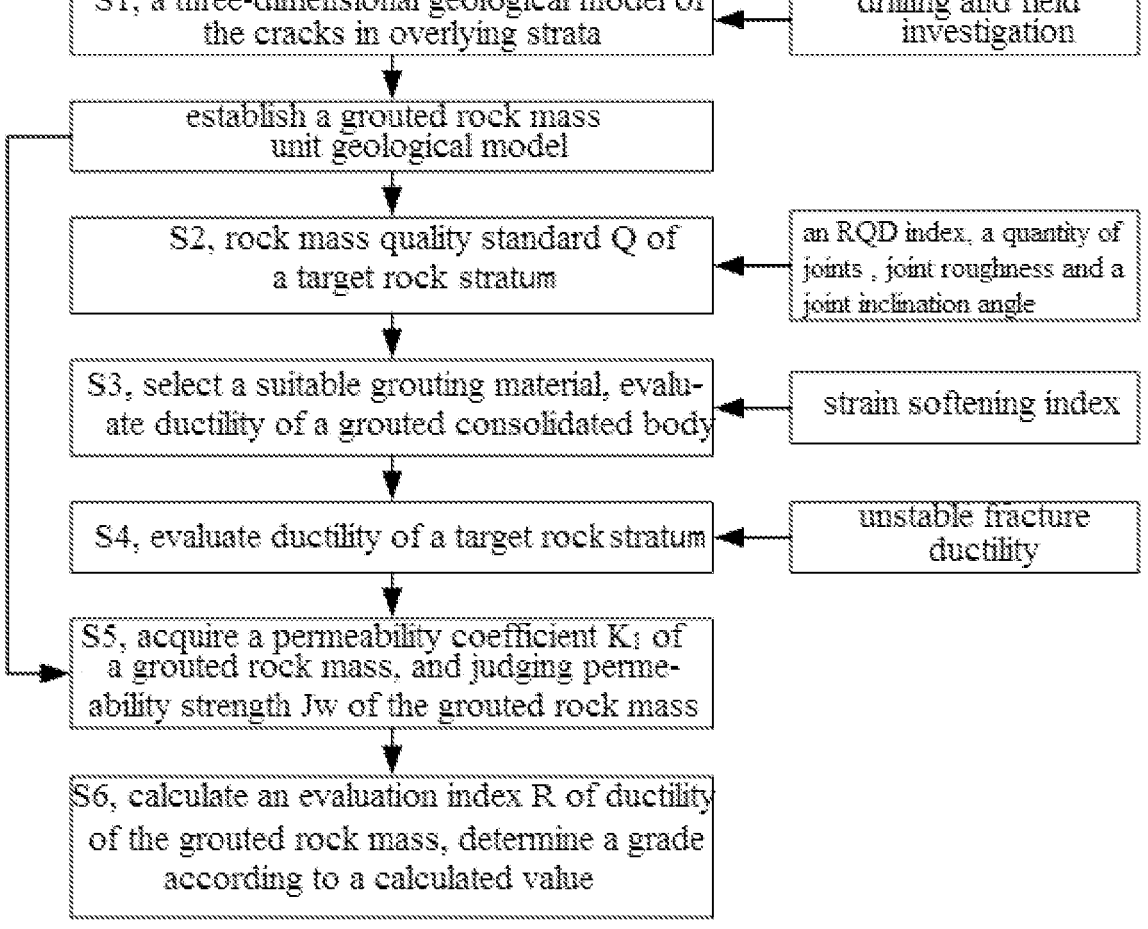

S1, a three-dimensional geological model of the cracks in overlying strata ◄──── drilling and field investigation establish a grouted rock mass unit geological model S2, rock mass quality standard Q of a target rock stratum ◄──── an RQD index, a quantity of joints , joint roughness and a joint inclination angle S3, select a suitable grouting material, evaluate ductility of a grouted consolidated body ◄──── strain softening index S4, evaluate ductility of a target rock stratum ◄──── unstable fracture ductility S5, acquire a permeability coefficient $K_1$ of a grouted rock mass, and judging permeability strength Jw of the grouted rock mass S6, calculate an evaluation index R of ductility of the grouted rock mass, determine a grade according to a calculated value

1

EVALUATION METHOD OF DUCTILITY OF GROUTED ROCK MASS FOR ADVANCED RENOVATION OF WATER-SAND MIXTURE INRUSH AREA

CROSS REFERENCE TO RELATED APPLICATION

This patent application claims the benefit and priority of Chinese Patent Application No. 202211376588.1, filed on Nov. 4, 2022 the disclosure of which is incorporated by reference herein in its entirety as part of the present application.

TECHNICAL FIELD

The present disclosure relate to the technical field of mines, and in particular to an evaluation method of ductility of a grouted rock mass for advanced renovation of a water-sand mixture inrush prevention area.

BACKGROUND

In large-scale, high-intensity coal mining, there are major geological disasters such as large-scale seam roof cutting and water-sand mixture inrush, and environmental damage problems such as soil erosion. In particular, the water-sand mixture inrush will cause property losses and casualties, which will seriously affect mine safety production.

The water-sand mixture inrush is a mine geological disaster in which water-sand mixture fluid with high sand content bursts into the underground working face when mining near a loose layer. The main reason causing the water-sand mixture inrush is that the aquifer and the bedrock weathering zone are prone to permeation deformation and damage under the effect of the overlying strata failure zone. Therefore, in order to ensure the safety of mining, grouting reconstruction and treatment projects are usually implemented for the working face and the overlying strata.

After the implementation of the grouting reconstruction projects, the related hydrogeological conditions, the engineering geological conditions of the overlying rock mass and the risk of water-sand mixture inrush have changed obviously. After grouting consolidation, the completion degree of the rock mass is excellent, showing a strong cementation state, and the strength of the rock mass is obviously improved. At the same time, different from the brittle deformation and failure of the rock itself, the grouted consolidated rock mass has certain ductility, which can well adapt to the large deformation during mining and reduce the harm of water-sand mixture inrush, so that the ductility of the grouted rock mass is very important for the mine safety production.

However, at present, there are few evaluation methods of the ductility of the grouted rock mass for advanced renovation of the water-sand mixture inrush prevention area. Some evaluation methods only consider grouting materials, rock mass lithology and other factors, while ignoring the interaction therebetween. The lack of influencing factors will directly lead to inaccurate evaluation, and some evaluation methods cannot quantify the results of ductility of the grouted rock mass and cannot accurately evaluate the ductility of the overlying rock mass after being grouted and consolidated.

SUMMARY

The objective of the present disclosure is to provide an evaluation method of ductility of a grouted rock mass for advanced renovation of a water-sand mixture inrush prevention area. The evaluation method not only integrates various factors to realize the evaluation of the ductility of the grouted rock mass, and avoids the inaccurate evaluation caused by the lack of influencing factors, but also realizes the quantification of the evaluation result, which is more reliable and reasonable.

In order to achieve the above objective, the evaluation method of ductility of a grouted rock mass for advanced renovation of a water-sand mixture inrush prevention area specifically includes following steps:

Step 1, acquiring a spatial distribution law of cracks in overlying strata, establishing a three-dimensional geological model of the cracks in overlying strata including a crack width and a horizontal inclination angle, and establishing a grouted rock mass unit geological model;

Step 2, calculating rock mass quality standard Q of a target rock stratum according to an RQD index, a quantity of joints $J_n$, joint roughness $J_r$ and a joint inclination angle $\alpha$ of each drill core of the target rock strata stratum;

Step 3, selecting a suitable grouting material, performing compression tests on a plurality of groups of grouted consolidated bodies by taking a strain softening index as a parameter for evaluating ductility of a grouted consolidated body, calculating a strain softening index $D_s$ of each group of the plurality of groups of grouted consolidated bodies, and obtaining an average value $D'_s$ of strain softening indexes $D_s$ of the plurality of groups of grouted consolidated bodies;

Step 4, selecting a plurality of groups of grouted target rock strata by taking unstable fracture ductility $$K_c^S$$

as a parameter for evaluating ductility of the target rock stratum, calculating unstable fracture ductility $$K_c^S$$

of each group of the plurality of groups of grouted target rock strata, and obtaining an average value $$K_C^{S'}$$

of the unstable fracture ductility $$K_c^S$$

of the plurality of groups of grouted target rock strata;

Step 5, acquiring a permeability coefficient $K_1$ of a grouted rock mass, and judging its permeability strength Jw of the grouted rock mass;

Step 6, calculating and obtaining an evaluation index R of ductility of the grouted rock mass, in which a formula for calculating the evaluation index R is as follows:

$$R = \frac{D'_s K_c^{S'}}{Q J_w}$$

determining a grade of the evaluation index R of ductility of the grouted rock mass according to a calculated value of the evaluation index R.

Furthermore, a formula for calculating the rock mass quality standard. Q of the target rock strata in step 2 is as follows:

$$Q = \frac{1}{N} \sum_{i=1}^{N} \left( \frac{RQD}{J_n} \frac{J_r}{\cos\alpha} \right)_i$$

where N is a quantity of boreholes in the target rock strata.

Furthermore, a formula for calculating the strain softening index $D_s$ of each group of the plurality of groups of grouted consolidated bodies in step 3 is as follows:

$$D_s = \frac{\Delta q}{\Delta \varepsilon_1}$$

where: $\Delta\varepsilon_1$ is an axial strain increment; $\Delta q$ is a corresponding increment of a deviator stress;

a formula for calculating the average value $D'_s$ of strain softening indexes $D_s$ of the plurality of groups of grouted consolidated bodies is as follows:

$$D'_s = \frac{1}{M} \sum_{i=1}^{M} D_{s_i}$$

where: M is a quantity of groups of compression tests on the plurality of groups of grouted consolidated bodies.

Furthermore, a formula for calculating the unstable fracture ductility $$K_c^S$$

in step 4 is as follows:

$$K_C^S = \frac{F_{Hmax} \times 10^{-3}}{th^{\frac{1}{2}}} f(\alpha_C)$$

$$\alpha_C = \frac{\alpha_0}{h}$$

$$f(\alpha_C) = \frac{A \times [B - C\alpha_C]}{(1 - \alpha_C)^{3/2}}$$

where $F_{Hmax}$ is a maximum horizontal load; t is a thickness of the grouted rock mass; h is a height of the grouted rock mass; $\alpha_0$ is an effective length of a grouted crack; A, B and C are test parameters;

a formula for calculating the average value $$K_C^{S'}$$

of the unstable fracture ductility $$K_c^S$$

of the plurality of groups of grouted target rock strata is as follows:

$$K_C^{S'} = \frac{1}{n} \sum_{i=1}^{n} K_{C_i}^S$$

where: n is a quantity of groups of the plurality of groups of grouted target rock strata.

Furthermore, the permeability strength Jw of the grouted rock mass in step 5 has a value range of:

$$J_w = \begin{cases} 1 & K_1 > 10^{-4} \text{ m/s} \\ 0.75 & 10^{-4} > K_1 > 10^{-5} \text{ m/s} \\ 0.5 & 10^{-7} > K_1 > 10^{-6} \text{ m/s} \\ 0.1 & 10^{-8} > K_1 > 10^{-7} \text{ m/s} \end{cases}$$

Furthermore, the evaluation index R of the ductility of the grouted rock mass is graded as follows:

when a value range of calculated R is $0 \leq R < 0.25$, it indicates that the ductility of the grouted rock mass is very good;

when a value range of calculated R is $0.25 \leq R < 0.5$, it indicates that the ductility of the grouted rock mass is good, when a value range of calculated R is $0.5 \leq R \leq 4.5$, it indicates that the ductility of the grouted rock mass is poor;

when a value range of calculated R is $R > 4.5$, it indicates that the ductility of the grouted rock mass is very poor.

Compared with the prior art, the evaluation method of ductility of the grouted rock mass for advanced renovation of the water-sand mixture inrush prevention area according to the present disclosure uses the quality parameters of the grouted rock mass to characterize the integrity of the rock mass and the proportion of the grouted body in the rock mass, uses the ductility of the grouted consolidated body to characterize the ductility of the grouted body, uses the fracture ductility of the intact rock stratum to characterize the instability strength of the rock stratum itself, and uses the permeability strength of the grouted rock mass to characterize the interaction between the rock stratum and the grouted body. The evaluation method integrates various factors described above to take the ductility of the grouted rock mass as the evaluation object, which can accurately evaluate the ductility of the overlying rock mass after being grouted and consolidated, and avoid the inaccurate evaluation caused by the lack of influencing factors. In addition, the calculation results of the evaluation index R of the ductility of the grouted rock mass are divided into four grades. The evaluation method can visually match the data with the results, and realize the quantification of the evaluation results, which is more reliable and reasonable.

BRIEF DESCRIPTION OF THE DRAWINGS

FIG. 1 is an overall schematic diagram of the present disclosure.

DETAILED DESCRIPTION OF THE EMBODIMENTS

The present disclosure will be further explained with reference to the attached drawings.

As shown in FIG. 1, an evaluation method of ductility of a grouted rock mass for advanced renovation of a water-sand mixture inrush prevention area specifically includes the following steps.

Step 1, a spatial distribution law of cracks in overlying strata is acquired, a three-dimensional geological model of the cracks in overlying strata including a crack width and a horizontal inclination angle is established, and a grouted rock mass unit geological model is established.

Specifically, for example, the spatial distribution law of cracks in overlying strata is acquired by methods such as drilling and field investigation.

The three-dimensional geological model can provide data for the subsequent target rock strata for such as calculating the RQD average value of the rock strata, and different areas can also be divided according to the rupture degree of the rock strata in the three-dimensional geological model, and the flexibility grade of the grouted rock mass in different regions can be evaluated, respectively;

The grouted rock mass unit geological model provides a geological model for the subsequent test of the permeability coefficient and the permeability strength of the grouted rock mass.

Step 2, according to an RQD index, a quantity of joints, joint roughness and a joint inclination angle of each drill core of a target rock stratum, the average RQD index, the average quantity of joints, the average joint roughness and the average joint inclination angle of the target rock stratum are obtained, and rock mass quality standard Q of the target rock strata is calculated.

Specifically, the RQD index of the drill core refers to the percentage of the cumulative length of drill cores with a length equal to or greater than 10 cm in the drill cores to the total length of drilling footage.

The porous drilling are performed on the target rock strata for grouting, and a statistic is performed on the samples of each borehole to obtain the RQD index, the quantity of joints $J_n$, the joint roughness $J_r$ and the joint inclination angle $\alpha$ of the drill core of each borehole.

The corresponding average value of a plurality of boreholes is calculated as follows:

$$RQD' = \frac{1}{N}\sum_{i=1}^{N}RQD_i$$

$$J_n' = \frac{1}{N}\sum_{i=1}^{N}J_{ni}$$

$$J_r' = \frac{1}{N}\sum_{i=1}^{N}J_{ri}$$

$$\alpha' = \frac{1}{N}\sum_{i=1}^{N}a_i$$

where: N is the quantity of boreholes in the target rock strata.

Furthermore, the formula for calculating the rock mass quality standard Q of the target rock strata is as follows:

$$Q = \frac{RQD'}{J_n'}\frac{J_r'}{\cos\alpha'}$$

or $$Q = \frac{1}{N}\sum_{i=1}^{N}\left(\frac{RQD}{J_n}\frac{J_r}{\cos\alpha}\right)_i$$

Step 3, a suitable grouting material is selected, compression tests are performed on a plurality of groups of grouted consolidated bodies to obtain a stress-strain curve of each of the plurality of groups of grouted consolidated bodies, the strain softening index $D_s$ of each of the plurality of groups of grouted consolidated bodies is calculated, and an average value $D'_s$ of the strain softening indexes $D_s$ of the plurality of groups of grouted consolidated bodies is obtained.

Specifically, the ductility of the grouted consolidated body is used to characterize the ductility of the grouted body itself, and the strain softening index $D_s$ is used to evaluate the ductility of the grouted consolidated body.

In the compression test, a plurality of groups of grouted consolidated bodies are selected, so as to avoid the problem that the calculation result error caused by a single test is large, and the stress-strain curve in each group of test results is obtained. The strain softening index $D_s$ of the grouted consolidated body refers to the slope of the 3% stress-strain curve which has been linearly fitted after the peak intensity of the stress-strain curve of the grouted consolidated body, and is configured for evaluating the strain softening degree of the grouted consolidated body. The corresponding calculation formula is as follows:

$$D_s = \frac{\Delta q}{\Delta\varepsilon_1}$$

where: $\Delta\varepsilon_1$ is an axial strain increment, which refers to the 3% strain after the peak strength of the stress-strain curve. $\Delta q$ is a corresponding increment of a deviator stress. The stress-strain curve of strain softening shows that $D_s$ should be negative. The smaller $D_s$ is, the greater the softening degree is, and to some extent, the greater the flexible deformation ability of the material can be projected.

Therefore, the formula for calculating an average value $$D'_s$$

of the strain softening indexes $D_s$ of the plurality of groups of grouted consolidated bodies is as follows:

$$D'_s = \frac{1}{M} \sum_{i=1}^{M} Ds_i$$

where: M is the quantity of groups of compression tests on the grouted consolidated bodies.

Step 4, a plurality of groups of grouted target rock strata are selected, unstable fracture ductility $$K_c^S$$

of each group of grouted target rock strata is calculated, and an average value $$K_C^{S'}$$

of the unstable fracture ductility $$K_c^S$$

of the plurality of groups of grouted target rock strata is obtained.

Specifically, the fracture ductility is a parameter that can characterize the properties of materials and the ductility of macro-crack propagation. The double-K fracture ductility criterion is a fracture model based on linear elastic fracture mechanics and combined with a virtual fracture model. The double-K fracture model includes a stress intensity factor K and a fracture ductility Kc. The two basic parameters, namely, K and Kc are used to describe the whole fracture process of rock materials.

The crack initiation ductility $$K_c^Q$$

is used to evaluate the ability of materials to resist the appearance of cracks. Generally, when the stress intensity factor of materials reaches the crack initiation ductility, materials begin to crack and enter the plastic deformation stage from the elastic deformation stage. The unstable fracture ductility $$K_c^S$$

is the limit value at which material cracks begin to expand unsteadily. When $$K_c^Q < K < K_c^S,$$

the cracks are in the stage of stable expansion.

For mining overlying strata, when the cracks in the rock mass reaches the stage of unstable expansion, the overlying strata completely loses its ductility and is destroyed, so that the unstable fracture ductility $$K_c^S$$

is used as a parameter to evaluate the ductility of the target rock stratum.

The formula for calculating the unstable fracture ductility $$K_c^S$$

is as follows:

$$K_C^S = \frac{F_{Hmax} \times 10^{-3}}{th^{\frac{1}{2}}} f(\alpha_C)$$

$$\alpha_C = \frac{\alpha_0}{h}$$

$$f(\alpha_C) = \frac{A \times [B - C\alpha_C]}{(1 - \alpha_C)^{3/2}}$$

where: $F_{Hmax}$ is a maximum horizontal load in unit of kN;
t is the thickness of the grouted rock mass in unit of m;
h is the height of the grouted rock mass in unit of m; $\alpha_0$ is the effective length of the grouted crack in unit of m;
A, B and C are test parameters.

Therefore, the formula for calculating the average value $$K_C^{S'}$$

of unstable fracture ductility $$K_c^S$$

of a plurality of groups of target rock strata is as follows:

$$K_C^{S'} = \frac{1}{n} \sum_{i=1}^{n} K_{C_i}^S$$

where: n is the quantity of groups of the grouted target rock strata.

Step 5, a permeability coefficient $K_1$ of a grouted rock mass is acquired, and the permeability strength Jw of the grouted rock mass is obtained.

Specifically, the hydraulic characteristics of the grouted rock mass can reflect the plugging effect of the grouted body, are affected by the rock stratum, the grouted body and their interaction on the joint surface and can effectively reflect the combination effect of the grouted body and the rock mass in some extent. Therefore, the permeability strength can be used to evaluate the permeability of the grouted rock mass.

Step 6, an evaluation index R of the ductility of the grouted rock mass is calculated, the formula for calculating the evaluation index R is as follows:

$$R = \frac{D'_s K^{S'}_c}{Q J_w}$$

According to the calculated value, the evaluation index R of the ductility of the grouted rock mass is graded. The For example, the value of the permeability strength Jw of the grouted rock mass is related to the permeability coefficient $K_1$ of the grouted rock mass, and its value range is as follows:

$$J_w = \begin{cases} 1 & K_1 > 10^{-4} \text{ m/s} \\ 0.75 & 10^{-4} > K_1 > 10^{-5} \text{ m/s} \\ 0.5 & 10^{-7} > K_1 > 10^{-6} \text{ m/s} \\ 0.1 & 10^{-8} > K_1 > 10^{-7} \text{ m/s} \end{cases}.$$

For example, the evaluation index R of the ductility of the grouted rock mass divides the flexibility of the rock mass into four grades: I, II, III and IV, as shown in Table 1.

Table 1: Grades of Ductility of the Grouted
Rock Mass

| grades | rock mass quality standard | | | | | | | | |
|---|---|---|---|---|---|---|---|---|---|
| | RQD value | $J_n$ | $J_r$ | joint inclination angle | Q | $D_s$ | $K_C{}^S$ | $J_w$ | R |
| I | 0-25 | <3 | 0-5 | 0-25 | 0-30 | 0-10 | <0.5 | 1 | 0-0.25 |
| II | 25-50 | 3-10 | 5-10 | 25-50 | 30-60 | 10-25 | 0.5-1.0 | 0.75 | 0.25-0.5 |
| III | 50-75 | 10-30 | 10-15 | 50-75 | 60-90 | 25-50 | 1.0-1.5 | 0.5 | 0.5-4.5 |
| IV | 75-100 | >34 | 15-20 | 75-90 | >90 | >50 | >1.5 | 0.1 | >4.5 | ductility of the grouted rock mass is mainly evaluated by the flexibility/ductility of the grouted rock mass.

For example, the rock mass quality standard Q of the target rock strata is divided into four grades, that is, when the value range of Q is 0≤Q<30, it indicates that the rock mass quality is good, and when the value range is 30≤Q<60, it indicates that the rock mass quality is average; when the value range is 60≤Q≤90, it indicates that the rock mass quality is poor; when the value range is >90, it indicates that the rock mass quality is very poor.

Specifically, the value range of RQD is 0-100, the value range of roughness $J_r$ is 0-20, and the value range of the joint inclination angle α is 0-90 degrees; and they are also graded.

Specifically, when the value range of RQD is 0≤RQD<25, it indicates that the rock quality is extremely poor, and when the range of RQD is 25≤RQD<50, it indicates that the rock quality is very poor; when the value range is 50≤RQD<75, it indicates that the rock quality is poor, and when the value range is 75≤RQD<100, it indicates that the rock quality is good.

$J_n$ is divided into four grades. When the value range is <3, it indicates that the integrity of the grouted rock mass is very good; when the value range is 3≤$J_n$<10, it indicates that the integrity of the grouted rock mass is good; when the value range is 10≤$J_n$<30, it indicates that the integrity of the grouted rock mass is poor; and when the value range is >30, it indicates that the grouted rock mass is in a broken state;

$J_r$ is divided into four grades. When the value range is 15≤$J_r$<20, the surface is very rough; when the value range is 10≤$J_r$<15, the surface is rough; when the value range is 5≤$j_r$<10, the surface is smooth; and when the value range is 0≤$J_r$<5, the surface is very smooth.

α is divided into four grades: 0≤α<25°, 25≤α<50°, 50≤α<75°, 75≤α<90°.

It is noted that the evaluation index R of the ductility of the grouted rock mass is graded as follows.

When the value range of calculated R is 0≤R<0.25, it indicates that the ductility of the grouted rock mass is grade I, and the ductility of the grouted rock mass is very good. In addition, when the value range of Q is 0≤Q<30, the value range of $D_s$ is 0≤$D_S$<10, and Jw is 1, it indicates that the quality of the grouted rock mass is good, the flexibility of the grouted body is good, and the interaction between the rock stratum and the grouted body is good.

When the value range of calculated R is 0.25≤R<0.5, it indicates that the ductility of the grouted rock mass is grade II, and the ductility of the grouted rock mass is good. In addition, when the value range of Q is 30≤Q<60, the value range of $D_s$ is 10≤Ds<25, and Jw is 0.75, it indicates that the quality of the grouted rock mass is average, the flexibility of the grouted body is average, and the interaction between the rock stratum and the grouted body is average.

When the value range of calculated R is 0.5≤R≤4.5, it indicates that the ductility of the grouted rock mass is grade III, and the ductility of the grouted rock mass is poor. In addition, when the value range of Q is 60≤Q≤90, the value range of $D_s$ is 25≤Ds<50, and Jw is 0.5, it indicates that the quality of the grouted rock mass is poor, the flexibility of the grouted body is poor, and the interaction between the rock stratum and the grouted body is poor.

When the value range of calculated R is R>4.5, it indicates that the ductility of the grouted rock mass is grade IV, and the ductility of the grouted rock mass is very poor. In addition, when the value range of Q is >90, the value range of $D_s$ is >50, and Jw is 0.1, it indicates that the quality of the grouted rock mass is very poor, the flexibility of the grouted body is very poor, and the interaction between the rock stratum and the grouted body is very poor.

The present disclosure provides to an evaluation method of ductility of a grouted rock mass for advance renovation of a water-sand mixture inrush prevention area, which integrates the quality of the rock mass, the properties of the rock stratum itself, the ductility of the grouted consolidated body and the permeability strength of the grouted rock mass, so as to quantify the evaluation index R of the ductility of the grouted rock mass.

That is, the evaluation method uses the quality parameters of the grouted rock mass to characterize the integrity of the rock mass and the proportion of the grouted body in the rock mass, uses the ductility of the grouted consolidated body to characterize the ductility of the grouted body, uses the fracture ductility of the intact rock stratum to characterize the instability strength of the rock stratum itself, and uses the permeability strength of the grouted rock mass to characterize the interaction between the rock stratum and the grouted body. The evaluation method integrates various factors described above to take the ductility of the grouted rock mass as the evaluation object, which can accurately evaluate the ductility of the overlying rock mass after being grouted and consolidated, and avoid the inaccurate evaluation caused by the lack of influencing factors.

In addition, the calculation results of the evaluation index R of the ductility of the grouted rock mass are divided into four grades, which can visually match the data with the results and make the evaluation more visual; the rock mass quality standard Q of the target rock strata is calculated with reference to the RQD index, the quantity of joints $J_n$, the joint roughness $J_r$ and the a joint inclination angle $\alpha$ of the drill core, and its influence on the strength and the integrity of the rock mass can be considered in many factors.

What is claimed is:

1. An evaluation method of ductility of a grouted rock stratum for advanced renovation of a water-sand mixture inrush prevention area, comprising following steps:

Step 1, acquiring a spatial distribution law of cracks in overlying strata, establishing a three-dimensional geological model of the cracks in overlying strata including a crack width and a horizontal inclination angle, and establishing a grouted rock stratum unit geological model;

Step 2, calculating rock stratum quality standard Q of a target rock stratum in the overlying strata according to an RQD index, a quantity of joints $J_n$, joint roughness $J_r$ and a joint inclination angle $\alpha$ of each drill core of the target rock stratum by means of $$Q = \frac{1}{N}\sum_{i=1}^{N}\left(\frac{RQD}{J_n}\frac{J_r}{\cos\alpha}\right)_i$$

wherein N is a quantity of boreholes in the target rock strata;

Step 3, solidifying a grouting material to obtain a plurality of groups of grouting consolidated bodies, performing compression tests on the plurality of groups of grouting consolidated bodies, calculating a strain softening index $D_s$ of each of the plurality of groups of grouted consolidated bodies, taking the strain softening index $D_s$ as a parameter for evaluating ductility of each of the plurality of groups of grouted consolidated bodies, and obtaining an average value $D'_s$ of strain softening indexes $D_s$ of the plurality of groups of grouted consolidated bodies;

Step 4, grouting the grouting material into the target rock stratum, selecting a plurality of groups of grouted target rock in the grouted target rock stratum, calculating unstable fracture ductility $K_C^S$ of each of the plurality of groups of grouted target rocks, taking the unstable fracture ductility $K_C^S$ as a parameter for evaluating ductility of each of the plurality of groups of target rocks, and obtaining an average value $K_C^S$ of the unstable fracture ductilities $K_C^S$ of the plurality of groups of grouted target rock;

Step 5, acquiring a permeability coefficient $K_1$ of a grouted target rock stratum, and judging permeability strength Jw of the grouted target rock stratum;

Step 6, calculating and obtaining an evaluation index R of ductility of the grouted target rock stratum, wherein a formula for calculating the evaluation index R is as follows:

$$R = \frac{D'_s K_c^{S'}}{QJ_w}$$

determining a grade of the evaluation index R of ductility of the grouted target rock stratum according to a calculated value of the evaluation index R, wherein the evaluation index R of the ductility of the grouted target rock stratum is graded as follows:

when a value range of calculated R is $0 \leq R < 0.25$, it indicates that the ductility of the grouted target rock stratum is very good;

when a value range of calculated R is $0.25 \leq R < 0.5$, it indicates that the ductility of the grouted target rock stratum is good;

when a value range of calculated R is $0.5 \leq R \leq 4.5$, it indicates that the ductility of the grouted target rock stratum is poor;

when a value range of calculated R is $R > 4.5$, it indicates that the ductility of the grouted target rock stratum is very poor.

2. The evaluation method of ductility of the grouted rock stratum for advanced renovation of the water-sand mixture inrush prevention area according to claim 1, wherein a formula for calculating the strain softening index $D_s$ of each of the plurality of groups of grouting consolidated bodies in step 3 is as follows:

$$D_s = \frac{\Delta q}{\Delta \varepsilon_1}$$

wherein $\Delta\varepsilon_1$ is an axial strain increment; $\Delta q$ is a corresponding increment of a deviator stress;

a formula for calculating the average value $D'_s$ of strain softening indexes $D_s$ of the plurality of groups of grouting consolidated bodies is as follows:

$$D'_s = \frac{1}{M}\sum_{i=1}^{M}D_{s_i}$$

wherein M is a quantity of groups of compression tests on the plurality of groups of grouted consolidated bodies.

3. The evaluation method of ductility of the grouted rock stratum for advanced renovation of the water-sand mixture inrush prevention area according to claim 2, wherein the permeability strength Jw of the grouted target rock stratum in step 5 has a value range of:

$$J_w = \begin{cases} 1 & K_1 > 10^{-4} \text{ m/s} \\ 0.75 & 10^{-4} > K_1 > 10^{-5} \text{ m/s} \\ 0.5 & 10^{-7} > K_1 > 10^{-6} \text{ m/s} \\ 0.1 & 10^{-8} > K_1 > 10^{-7} \text{ m/s} \end{cases}.$$

5

10

\* \* \* \* \*